(12) United States Patent
Davis

(10) Patent No.: US 7,087,627 B1
(45) Date of Patent: Aug. 8, 2006

(54) COMBINATIONS FOR THE TREATMENT OF DISEASES INVOLVING ANGIOGENESIS

(75) Inventor: Peter David Davis, Watlington (GB)

(73) Assignee: Angiogene Pharmaceuticals Ltd., Watlington (GB)

( * ) Notice: Subject to any disclaimer, the term of this patent is extended or adjusted under 35 U.S.C. 154(b) by 0 days.

(21) Appl. No.: 09/890,989

(22) PCT Filed: Feb. 15, 2000

(86) PCT No.: PCT/GB00/00511

§ 371 (c)(1),
(2), (4) Date: Dec. 14, 2001

(87) PCT Pub. No.: WO00/48591

PCT Pub. Date: Aug. 24, 2000

(30) Foreign Application Priority Data

Feb. 16, 1999 (GB) ................................ 9903404.3

(51) Int. Cl.
*A61K 31/44* (2006.01)
(52) U.S. Cl. .................. 514/339; 514/418; 514/227.2; 544/253
(58) Field of Classification Search ............ 514/227.2, 514/310, 217.11, 224.2, 339, 418; 544/253, 544/47, 48, 50, 90, 91
See application file for complete search history.

(56) References Cited

FOREIGN PATENT DOCUMENTS

| WO | 9412165 | 6/1994 |
|----|---------|--------|
| WO | 9501972 | 1/1995 |
| WO | 9509621 | 4/1995 |
| WO | 9618617 | 6/1996 |
| WO | 9732585 | 1/1997 |
| WO | 9830537 | 7/1998 |

OTHER PUBLICATIONS

Tozer et al., Cancer Res. (1999), 59(7), 1626-1634.*
Stenger et al. (Eur. J. Pharmacol. 1995, 294, 703-12, see abstract only).*
Narayanan et al (J. Biol. Chem. 1995, 270, 11103-10, see abstract only).*
Blank M et al (Photochem Photobiol Sep. 2002;76: 335-40, abstract only with this Office Action).*
Bonfoco et al (1995, Experimental Cell Research, vol. 218, pp. 189-200).*
Ohsumi et al., J Med Chem. Jul. 30, 1998;41(16):3022-32.*
Moilanen, E. et al. "Persistent Induction of Nitric Oxide . . . Acid" British J. of Cancer. vol. 77, No. 3, p. 426-433, (1988).
Chaplin, D.J. et al. "Modification of Tumor Blood Flow . . . Directions" Seminars in Radiation Oncology, vol. 8, No. 3, p. 151-163, (1998).
Effect of the Tumor Vascular-Damaging Agent, ZD6126, on the Radioresponse of U87. Glioblastoma: Clinical Cancer Research vol. 11 835-842, 2005: Phyllis R. Wachsberger, Randy Burd, nichol Marero, Constantine Daskalakis, Anderson Ryan, Peter McCue, Adam P. Dicker.
Annex A—Combretastatin A-4 Phosphate as a Tumor Vascular-Targeting Agent: Early Effects in Tumors and Normal Tissues: Tozer, Prise, Wilson, Locke, Vojnovic, Stratford, Dennis, Chaplin: Cancer Research 59, 1626-1634, Apr. 1, 1999.
Annex B—Enhancement of Vascular Targeting by Inhibitors of Nitric Oxide Synthase: Davis, Tozer, Naylor, Thomson, Lewis, Hill: Int. J. Radiation Onocology Biol. Phys. vol. 54, No. 5 pp. 1532-1536, 2002.
Annex C—Effect of the tumor vascular damaging agent, ZD6126 on the radioresponse of U97 glioblastoma: Wachsberger, Burd, Marrrero, Daskalakis, Ryan, McCue, Dicker.

* cited by examiner

*Primary Examiner*—Misook Yu
(74) *Attorney, Agent, or Firm*—Ladas & Parry LLP

(57) ABSTRACT

Compositions for the inhibition of the formation of new vasculature by angiogenesis are provided comprising the combination of a vasculature damaging agent and an inhibitor of the formation or action of nitric oxide in mammalian systems. There are also provided the use of said combinations in medicaments and kits of said compounds and treatment employing said materials.

19 Claims, No Drawings

COMBINATIONS FOR THE TREATMENT OF DISEASES INVOLVING ANGIOGENESIS

This invention relates to a method for treating diseases involving active angiogenesis, to compositions useful for the treatment of diseases involving angiogenesis and to the use of the compositions in the preparation of a medicament for the treatment of diseases involving active angiogenesis. In one aspect of the invention the method involves the administration to a mammal of an inhibitor of nitric oxide in combination with a compound inducing vascular damage.

Formation of new vasculature by angiogenesis is a key pathological feature of several diseases (J Folkman, New England Journal of Medicine 333, 1757–1763, 1995). For example, for a solid tumour to grow it must develop its own blood supply upon which it depends critically for the provision of oxygen and nutrients; if this blood supply is mechanically shut off the tumour undergoes necrotic death. Neovascularisation is also a clinical feature of skin lesions in psoriasis, of the invasive pannus in the joints of rheumatoid arthritis patients and of atherosclerotic plaques. Retinal neovascularisation is pathological in macular degeneration and in diabetic retinopathy. In all these diseases reversal of neovascularisation by damaging the newly-formed vascular endothelium is expected to have a beneficial therapeutic effect.

Certain chemical compounds have been shown to have vascular damaging activity against the newly formed endothelium of solid tumours. These agents include, for example, combretastatin A4 phosphate (Dark et al., Cancer Research 57, 1829–1834, 1997), combretastain analogues (for example those described in J Med Chem 41 3022–32, 1998 by Ohsumi et al.), the flavone acetic acids, for example 5,6-dimethylxanthenone acetic acid (Zwi, Pathology, 26, 161–9, 1994), colchicine (Baguley et al. Eur J Cancer 27, 482–7, 1991). However some tumours are resistant to these agents.

One characteristic of tumours relatively resistant to vascular damaging agents is their ability to produce large amounts of nitric oxide. The role of nitric oxide in tumour growth is unclear and there have been reports of both tumor-stimulating and tumour inhibiting effects (Chinje and Stratford, Essays Biochem. 32,61–72, 1997). It has been suggested that the antitumour effects of 5,6-dimethylxanthenone acetic acid are mediated in part by nitric oxide production (Thompsen et al. Cancer Chemother Pharmacol. 31, 151–5, 1992).

WO-A 9509621 and Br. J. Cancer (1998), 77(3), 426–433 disclose combinations of cytokine releasing anticancer agents (TNF-releasing agents). These relate to ameliorating the effects of pro-inflammatory cytokines. There is no suggestion of synergistic activity from a combination of a vascular damaging agent (many of which have no pro-inflammatory activity) and an NO inhibitor.

We have found that the efficacy of vascular damaging agents can be improved by combining the treatment with inhibitors of the formation or action of nitric oxide in a mammalian system.

In particular the efficacy of vascular damaging agents can be improved by combination with inhibitors of nitric oxide synthases, the enzymes that produce nitric oxide from arginine. In particular the efficacy of vascular damaging agents against tumours relatively resistant to their effects is improved by treatment with a nitric oxide synthase inhibitor.

Accordingly in one aspect of the invention we provide a method of treatment for a mammal having a disease that involves active angiogenesis such method comprising the administration of a therapeutic or subtherapeutic amount of a vascular damaging agent together with an inhibitor of nitric oxide synthase in an amount sufficient to augment the effect of the vascular damaging agent. The method is useful for the treatment of diseases such as cancers, especially solid tumours, psoriasis, diabetic retinopathy, macular degeneration, atherosclerosis and rheumatoid arthritis.

The vascular damaging agent and the nitric oxide synthase inhibitor can be administered together or separately. The method may be used as a sole therapy or in combination with other treatments. For the treatment of solid tumours compounds of the invention may be administered in combination with radiotherapy or in combination with other anti-tumor substances for example those selected from mitotic inhibitors, for example vinblastine, paclitaxel and docetaxel; alkylating agents, for example cisplatin, carboplatin and cyclophosphamide, antimetabolites, for example 5-fluorouracil, cytosine arabinoside and hydroxyurea, intercalating agents for example adriamycin and bleomycin; enzymes, for example asparaginase; topoisomerase inhibitors for example etoposide, topotecan and irinotecan; thymidylate synthase inhibitors for example raltitrexed; biological response modifiers for example interferon; antibodies for example edrecolomab; and anti-hormones for example tamoxifen. Such combination treatment may involve simultaneous or sequential application of the individual components of the treatment.

The vascular damaging agent and the nitric oxide synthase inhibitor can be administered by the same route or by different routes. Such routes of administration include oral, buccal, nasal, topical, rectal and parenteral administration. Each component of the method, the vascular damaging agent and the nitric oxide synthase inhibitor may independently be administered in a form suitable for the intended route of administration and such forms may be prepared in a conventional manner using conventional excipients. For example for oral administration the pharmaceutical compositions may take the form of tablets or capsules. For nasal administration or administration by inhalation the compounds may be conveniently delivered as a powder or in solution. Topical administration may be as an ointment or cream and rectal administration may be as a suppository. For parenteral injection (including intravenous, subcutaneous, intramuscular, intravascular or infusion) the composition may take the form of, for example, a sterile solution, suspension or emulsion. The preferred route of administration of each component will depend on the disease being treated. For solid tumours the components may each advantageously be delivered, either together or separately, as an intravenous infusion.

Vascular damaging agents are compounds which induce selective damage to newly formed, rather than established, vasculature. Many such compounds are known and it is considered this invention is generally applicable to such agents. Such agents include tubulin-binding agents, for example the combretastatins and their prodrugs, the colchinols and their prodrugs and (Z)-2-methoxy-5-[2-(3,4,5-trimethoxyphenyl)vinyl]phenylamine and its prodrugs, TNF-alpha inducing agents such as the xanthenone acetic acids, for example dimethylxanthenoneacetic acid, and antibodies targeted to the vasculature.

A wide variety of compounds which inhibit the formation or action of nitric oxide in mammalian systems can be employed. Specifically nitric oxide synthase inhibitors are those compounds which inhibit any of the forms of nitric oxide synthase. Such agents include derivatives of arginine, ornithine, lysine and citrulline, S-alkylthioureas and aminoguanidines. Where the nitric oxide synthase inhibitor is a derivative of arginine it may be, for example, an $N^G$-substituted L-arginine selected from $N^G$-nitro-L-arginine and alkyl esters thereof, $N^G$-methyl-L-arginine and $N^G$-amino-L-arginine. Where the nitric oxide synthase inhibitor is a derivative of ornithine it may be, for example L-N6-(1-iminoethyl)-ornithine. Where the nitric oxide synthase inhibitor is a derivative of lysine it may be, for example L-N6-(1-iminoethyl)-lysine. Where the nitric oxide synthase inhibitor is a derivative of citrulline it may be, for example L-thiocitrulline, L-homothiocitrulline or an S-alkylthiocitrulline such as S-methyl-L-thiocitrulline.

In a further embodiment of the invention there is provided a composition for the treatment of diseases involving active angiogenesis. The composition of the invention comprises a vascular damaging agent in combination with a nitric oxide synthase inhibitor where both the vascular damaging agent and the nitric oxide synthase inhibitor are as hereinbefore defined.

Thus for example the composition may contain for example a combretastatin derivative, a colchicine derivative, a colchinol derivative, a xanthenone acetic acid derivative or a vascular targeted antibody, in combination with a nitric oxide synthase inhibitor for example a derivative of arginine, a derivative of ornithine, a derivative of lysine, a derivative of citrulline, a S-alkylthioureas or an aminoguanidine.

Particular examples of vascular damaging agents that may be present in the composition include combretastatin A4 and its prodrugs for example combretastatin A4 phosphate, (Z)-2-methoxy-5-[2-(3,4,5-trimethoxyphenyl)vinyl]phenylamine and its prodrugs, N-acetylcolchinol and its prodrugs for example N-acetylcolchinol-O-phosphate and 5,6-dimethylxanthenoneacetic acid.

Particular examples of nitric oxide synthase inhibitors which may be present in the composition include derivatives of arginine, ornithine, lysine and citrulline, S-alkylthioureas aminoguanidines and aminopyridines. Where the nitric oxide synthase inhibitor is a derivative of arginine it may be, for example, an $N^G$-substituted L-arginine selected from $N^G$-nitro-L-arginine and alkyl esters thereof, $N^G$-methyl-L-arginine and $N^G$-amino-L-arginine. Where the nitric oxide synthase inhibitor is a derivative of ornithine it may be, for example L-N6-(1-iminoethyl)-ornithine. Where the nitric oxide synthase inhibitor is a derivative of lysine it may be, for example L-N6-(1-iminoethyl)-lysine. Where the nitric oxide synthase inhibitor is a derivative of citrulline it may be, for example L-thiocitrulline, L-homothiocitrulline or an S-alkylthiocitrulline such as S-methyl-L-thiocitrulline. Where the nitric oxide synthase inhibitor is an aminopyridine it may be for example 2-amino-4-methylpyridine.

The composition is useful for the treatment of diseases involving active angiogenesis for example solid tumours, psoriasis, diabetic retinopathy, macular degeneration, atherosclerosis and rheumatoid arthritis.

The relative proportion of each component will be determined by the identity of each individual vascular damaging agent or nitric oxide synthase inhibitor and by the disease to be treated.

The composition may include pharmaceutically acceptable excipients selected with regard to the intended route of administration and standard pharmaceutical practice. The composition may take a form suitable for oral, buccal, nasal, topical, rectal or parenteral administration and may be prepared in a conventional manner using conventional excipients. For example for oral administration the composition may take the form of tablets or capsules. For nasal administration or administration by inhalation the compounds may be conveniently delivered as a powder or in solution. Topical administration may be as an ointment or cream and rectal administration may be as a suppository. For parenteral injection (including intravenous, subcutaneous, intramuscular, intravascular or infusion) the composition may take the form of, for example, a sterile solution, suspension or emulsion.

The dose of a compound of the invention required for the prophylaxis or treatment of a particular condition will vary depending on the identity of the individual components, the route of administration, the form and severity of the condition and whether the compound is to be administered alone or in combination with another drug. Thus the precise dose will be determined by the administering physician and will depend on the particular vascular damaging agent and NO synthase inhibitor in the composition. However the dose of the vascular damaging agent envisaged is, for example, in the range 10–1000 mg/m² body surface, preferably 20–200 mg/m² and that for the nitric oxide inhibitor 1–1000 mg/m², preferably 5–500 mg/m². A unit dose form of the vascular damaging agent as, for example, a sterile solution for injection will usually I contain, for example, 40–400 mg of the active ingredient. A unit dose form of the nitric oxide synthase inhibitor as, for example, a sterile solution for injection will usually contain, for example, 10–1000 mg of the active ingredient. A unit dose form of a composition containing both a vascular damaging agent and a nitric oxide synthase inhibitor as, for example, a sterile solution for injection will usually contain, for example, 40–400 mg of the vascular damaging agent and 10–1000 mg of the nitric oxide synthase inhibitor.

The composition of the invention may be administered as a sole therapy or in combination with other treatments. For the treatment of solid tumours the composition may be administered in combination with radiotherapy or in combination with other anti-tumour substances for example those selected from mitotic inhibitors, for example vinblastine, paclitaxel and docetaxel; alkylating agents, for example cisplatin, carboplatin and cyclophosphamide; antimetabolites, for example 5-fluorouracil, cytosine arabinoside and hydroxyurea; intercalating agents for example adriamycin and bleomycin; enzymes, for example aspariginase; topoisomerase inhibitors for example etoposide, topotecan and irinotecan; thymidylate synthase inhibitors for example raltitrexed; biological response modifiers for example interferon; antibodies for example edrecolomab; and anti-hormones for example tamoxifen. Such combination treatment may involve simultaneous or sequential application of the individual components of the treatment.

In a further embodiment of the invention we provide the use of a compostion of the invention for the preparation of a medicament for the treatment of a disease involving active angiogenesis.

The invention will now be illustrated by the following Examples in which biological assays are used to illustrate the invention:

Induction of Necrosis

Mice bearing either CaNT or SaS tumours were treated with the test compound and tumours excised after 24 h, fixed in formalin, embedded in paraffin, sectioned and stained with haematoxylin and eosin. Sections were scored based on area of necrosis as follows:

| % necrosis | score | % necrosis | score |
|---|---|---|---|
| 0–10 | 1 | 51–60 | 6 |
| 11–20 | 2 | 61–70 | 7 |
| 21–30 | 3 | 71–80 | 8 |
| 31–40 | 4 | 81–90 | 9 |
| 41–50 | 5 | 91–100 | 10 |

Control tumours had mean scores of 2.0 (CaNT) and 1.0 (SaS).

EXAMPLE 1

In this assay the effect of a given dose of either a vascular damaging agent or a nitric oxide synthase inhibitor administered alone can be compared with the effect of a combination of the two agents.

TABLE 1

Enhancement of Combretastatin A4 phosphate (CA4P) activity in SaS tumours by coadministration of L-$N^\alpha$-nitroarginine (L-NNA)

| Treatment | Necrosis score ± SEM (n) |
|---|---|
| None | 1.0 ± 0 (10) |
| CA4P, 500 mg/kg | 1.7 ± 0.7 (3) |
| L-NNA, 10 mg/kg | 2.0 ± 1 (3) |
| CA4P, 500 mg/kg + L-NNA 10 mg/kg | 9.0 ± 0 (3) |

EXAMPLE 2

TABLE 2

Enhancement of Combretastatin A4 phosphate (CA4P) activity in SaS tumours by coadministration of 2-amino-4-methylpyridine (AMP)

| Treatment | Necrosis score ± SEM (n) |
|---|---|
| None | 1.0 ± 0 (10) |
| CA4P, 500 mg/kg | 1.7 ± 0.7 (3) |
| AMP, 10 mg/kg | 1.0 (2) |
| CA4P, 500 mg/kg + AMP 10 mg/kg | 4.5 (2) |

EXAMPLE 3

Activity Against Tumour Vasculature Measured by Fluorescent Dye.

The following experiment further demonstrates the ability of the compounds to damage tumour vasculature.

Tumour functional vascular volume in CaNT tumour-bearing mice was measured using the fluorescent dye Hoechst 33342 according to the method of Smith et al (Brit J Cancer 57, 247–253, 1988). The fluorescent dye was dissolved in saline at 6.25 mg/ml and injected intravenously at 10 mg/kg 24 hours after intra peritoneal drug treatment. One minute later, animals were killed and tumours excised and frozen; 10 μm sections were cut at 3 different levels and observed under UV illumination using an Olympus microscope equipped with epifluorescence. Blood vessels were identified by their fluorescent outlines and vascular volume was quantified using a point scoring system based on that described by Chalkley, (J Natl Cancer Inst, 4, 47–53, 1943). All estimates were based on counting a minimum of 100 fields from sections cut at the 3 different levels.

Table 3: Enhancement of Combretastatin A4 Phosphate (CA4P) Activity in CaNT Tumours by Coadministration of L-$N^g$-nitroarginine (L-NNA).

| Treatment | Vascular Volume % ± SEM (n) |
|---|---|
| None | 2.35 |
| CA4P, 25 mg/kg | 1.03 ± 0.14 (4) |
| L-NNA, 10 mg/kg | 2.45 ± 0.04 (3) |
| CA4P, 25 mg/kg + L-NNA 10 mg/kg | 0.63 ± 0.25 (3) |

The invention claimed is:

1. A method of treatment for a mammal having a disease involving active angiogenesis with the formation of new vasculature in the mammal, said method comprising administration to the mammal of a tubulin binding agent and an inhibitor of formation of nitric oxide, the tubulin binding agent being administered to the mammal in an amount effective to cause damage to the new vasculature, the inhibitor of formation of nitric oxide being administered to the mammal in an amount sufficient to augment the effect of the tubulin binding agent.

2. A method according to claim 1 wherein the tubulin binding agent and inhibitor of the formation of nitric oxide are administered substantially simultaneously but separately to the mammal under treatment.

3. A method of treatment for a mammal having a cancer involving a solid tumor, said method comprising administration of a tubulin binding agent and an inhibitor of the formation of nitric oxide in an amount sufficient to augment the effect of the tubulin binding agent.

4. A method according to claim 3 wherein the tubulin binding agent and the inhibitor of the formation of nitric oxide are administered substantially simultaneously but separately to the mammal under treatment.

5. A previously presented) A method according to claim 1 or claim 3 wherein the inhibitor of the formation of nitric oxide is an inhibitor of nitric oxide synthase.

6. A method according to claim 5 wherein the inhibitor of nitric oxide synthase is selected from the group consisting of a derivative of arginine, ornithine, lysine, citrulline, S-alkylthioureas and aminoguanidine.

7. A method according to claim 5 wherein the inhibitor of nitric oxide synthase is an $N^G$-substituted L-arginine selected from the group consisting of $N^G$-nitro-L-arginine and alkyl esters thereof, $N^G$-methyl-L-arginine and $N^G$-amino-L-arginine.

8. A method according to claim 6 wherein the derivative of ornithine is L-N6-(1-iminoethyl)-ornithine.

9. A method according to claim 6 wherein the derivative of lysine is L-N6-(1-iminoethyl)-lysine.

10. A method according to claim 6 wherein the derivative of citrulline is selected from the group consisting of L-thiocitrulline, L-homothiocitrulline and an S-alkylthiocitrulline.

11. A method according to claim 5 wherein the inhibitor of nitric oxide synthase is an aminopyridine.

12. A method according to claim 5 wherein the inhibitor of nitric oxide synthase is 2-amino-4-methylpyridine.

13. A method according to claim 1 or claim 3 wherein the tubulin binding agent is selected from the group consisting of N-acetylcolchinol and its prodrugs.

14. A method according to claim 1 or claim 3 wherein the tubulin binding agent is N-acetylcolchinol-O-phosphate.

15. A method according to claim 1 or claim 3 wherein the tubulin binding agent is selected from the group consisting of combretastin A4 and its prodrugs.

16. A method according to claim 1 or claim 3 wherein the tubulin binding agent is selected from the group consisting of combretastain A4 phosphate.

17. A method according to claim 1 or claim 3 wherein the tubulin binding agent is selected from the group consisting of (Z)-2-methoxy-5-[2-(3,4,5-trimethoxyphenyl)vinyl] phenylamine and its prodrugs.

18. A method according to claim 5 wherein the tubulin binding agent is selected from the group consisting of N-acetylcolchinol and its prodrugs, and combretastatin A4 and its prodrugs and wherein the inhibitor of nitric oxide synthase is selected from the group consisting of $N^G$-nitro-L-arginine or an alkyl ester thereof, $N^G$-methyl-L-arginine, $N^G$-amino-L-arginine, L-N6-(1-iminoethyl)-ornithine, LN6-(1-iminoethyl)-lysine, L-ihiocitrulline, L-homothiocitrulline, S-alkylthiocitrulline and 2-amino-4-methylpyridine.

19. A method according to claim 5 wherein the tubulin binding agent is selected from the group consisting of N-acetylcolchinol and its prodrugs, and combretastatin A4 and its prodrugs, and wherein the inhibitor of nitric oxide synthase is selected from the group consisting of $N^G$-nitro-L-arginine or an alkyl ester thereof and 2-amino-4-methylpyridine.

* * * * *